United States Patent [19]

Humphreys et al.

[11] Patent Number: 4,681,945

[45] Date of Patent: Jul. 21, 1987

[54] PREPARATION OF SYMMETRICAL TETRACHLOROPYRIDINE FROM CHLORINATED β-(TRICHLOROMETHYL) PYRIDINES EMPLOYING A CATALYST

[75] Inventors: Paula L. Humphreys, San Ramon; Thomas J. Dietsche, Berkeley, both of Calif.

[73] Assignee: The Dow Chemical Company, Midland, Mich.

[21] Appl. No.: 648,109

[22] Filed: Sep. 7, 1984

Related U.S. Application Data

[63] Continuation-in-part of Ser. No. 431,515, Sep. 30, 1982, abandoned.

[51] Int. Cl.⁴ .......................................... C07D 213/26
[52] U.S. Cl. ................................... 546/345; 546/346
[58] Field of Search .............................. 546/345, 346

[56] References Cited

U.S. PATENT DOCUMENTS 4,256,894  3/1981  Dietsche et al. ................... 546/345

Primary Examiner—Alan L. Rotman

[57] ABSTRACT

Symmetrical tetrachloropyridine is prepared by contacting chlorinated β-(trichloromethyl)pyridines with chlorine in a liquid phase reaction in the presence of from 0.1 to 1.0 mole % of a catalyst.

1 Claim, No Drawings

PREPARATION OF SYMMETRICAL TETRACHLOROPYRIDINE FROM CHLORINATED β-(TRICHLOROMETHYL) PYRIDINES EMPLOYING A CATALYST

CROSS REFERENCE TO RELATED APPLICATION:

This application is a continuation-in-part of Ser. No. 431,515, filed Sept. 30, 1982 now abandoned.

BACKGROUND OF INVENTION

The present invention relates to the preparation of symmetrical tetrachloropyridine, i.e., 2,3,5,6-tetrachloropyridine, hereinafter referred to as "sym-tet", from chlorinated β-(trichloromethyl)pyridines in a catalyzed reaction.

Sym-tet is a well known compound useful as a chemical intermediate in the preparation of a variety of pesticides. Previous methods for preparing sym-tet include those described in U.S. Pat. Nos. 3,538,100; 3,186,994; 4,225,718 and 4,256,984. Sym-tet is produced according to U.S. Patent 3,186,994 by chlorinating, in the absence of a catalyst, a polychloro-α-(trichloromethyl)pyridine in the liquid or gas phase. According to U.S. Pat. No. 4,256,894, sym-tet is prepared by reacting a chloro substituted α-(trichloromethyl)pyridine in the liquid state with chlorine at temperatures of at least about 160° C. in the presence of a catalyst.

SUMMARY OF INVENTION

Briefly, in accordance with the present invention, sym-tet is prepared in good yield by contacting a chlorinated β-(trichloromethyl)pyridine with chlorine and from 0.1 to 1.0 mole % catalyst in a liquid phase reaction under conditions sufficient to form sym-tet. The reaction is conducted at a temperature of at least about 160° C. optionally at a superatmospheric pressure. The present process is preferably conducted in a continuous, cyclical operation to produce sym-tet in a commercially viable yield.

The present invention offers advantages over known methods of preparing sym-tet which include: (1) less formation of the by-product pentachloropyridine, and (2) an accelerated rate of reaction.

DETAILED DESCRIPTION OF THE INVENTION

In conducting the process of the present invention, gaseous chlorine is passed into a liquid chlorinated β-(trichloromethyl)pyridine starting material at a temperature of at least about 160° C. in the presence of a catalyst. An amount of chlorine gas reactant is employed that is sufficient to fully chlorinate the pyridine reactant to sym-tet. Usually at least an equimolar amount of chlorine is employed while an excess of up to about 10 molar proportions or more of chlorine per mole of pyridine starting material desirably being employed. The most suitable rate at which the chlorine gas is fed will vary with such factors as reaction temperature, pressure, reaction mixture volume, starting material, etc. and readily determinable to one skilled in the art.

A catalyst is added to the present reactants to accelerate the rate of reaction and any catalyst effective and compatible with the present process is considered to be within the scope of the present invention. Representative catalysts include, for example, Lewis acid type catalysts such as metals, metaloxyhalides or metallic halides capable of being converted to covalent metallic chlorides under the conditions of the chlorination reaction of the present invention. The Lewis acid type catalysts described in U.S. Pat. No. 4,256,894, which is incorporated herein by reference, are acceptable catalysts in the present invention. Generally, an effective amount of a catalyst is present when the catalyst is employed in an amount ranging from about 0.1 to 1 mole percent based on the amount of chlorinated β-(trichloromethyl)pyridine starting material. Preferably, a catalyst concentration of from 0.3 to 0.5 mole percent, most advantageously about 0.4 mole percent, is employed. Preferred catalysts are iron powder and $FeCl_3$. When iron powder is employed as the catalyst it reacts with $Cl_2$ in the reaction mixture to form $FeCl_3$ in situ.

While the pressure at which the present reaction is conducted is not critical, a superatmospheric pressure is preferably employed. Generally speaking, the higher the pressure, the faster the rate of formation of sym-tet. The present reaction is advantageously run at a pressure of from about 15 psig to about 1,000 psig and preferably from about 25 psig to about 400 psig. A particularly preferred pressure to run the present process is about 200 psig.

Chlorinated β-(trichloromethyl)pyridines employed as starting materials are all well known compounds and are represented by the following formula:

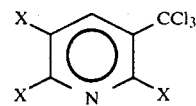

wherein each X independently represents H or Cl with the proviso that at least one X is always Cl. The chlorinated β-(trichloromethyl)pyridine starting materials may be supplied as pure compounds and reacted according to the present invention, or, as is usually the case, a mixture containing more than one chlorinated β-(trichloromethyl)pyridine compounds is reacted according to the present invention to form sym-tet. These mixtures of chlorinated β-(trichloromethyl)pyridines are obtained as by-products in the preparation of valuable β-(trichloromethyl)pyridines, such as, 2,3-dichloro-5-(trichloromethyl)pyridine and 2-chloro-5-(trichloromethyl)pyridine, which are chemical intermediates used in preparing herbicides.

In carrying out the present invention, the chlorinated β-(trichloromethyl)pyridine material, in the liquid form, is added to the reaction vessel. An effective amount of a catalyst is added to the reaction vessel and then the chlorine flow is commenced, usually at a sufficient rate to pressurize the reaction vessel to about 15 psig or more. The temperature of the reactants is then slowly increased to at least about 160° C. or more and the reaction maintained until sufficient amounts of sym-tet are obtained. Liquid samples from the reaction vessel and vent gases are periodically taken and analyzed employing known methods to monitor the course of the reaction. The reaction is terminated by stopping the heating of the reaction vessel and the flow of chlorine thereto and allowing the reaction vessel pressure to drop to atmospheric pressure. The desired sym-tet is then recovered employing known separatory or purification techniques such as distillation.

Alternatively the temperature of the reactants may be raised to the desired level before the introduction of chlorine gas begins.

If the present reaction is allowed to run too long formation of pentachloropyridine, a by-product, will result, thus decreasing the yield of sym-tet. It is readily apparent to one skilled in the art that the reaction be run for an amount of time which maximizes the yield of sym-tet. The optimum reaction time will depend on a variety of factors, such as, for example, specific starting materials employed, pressure, temperature, amounts of reactants employed, and rate of the chlorine feed, to name a few. Each operation of the present invention is monitored as described above to determine the optimum reaction time for that particular operation.

In one embodiment of the present invention one or more chlorinated $\beta$-(trichloromethyl)pyridines are reacted with chlorine in the presence of a catalyst at atmospheric pressure and at a temperature of at least about 160° C. For economical reasons, this reaction is preferably run at superatmospheric pressures usually from about 15 to about 220 psig or more, which increases the rate of the reaction. In a preferred embodiment, the reaction is conducted at temperatures of from about 160° C. to about 220° C. and pressures of about 100 psig to about 220 psig or more. In an especially preferred embodiment, a reaction temperature of about 200° C. and a reaction pressure of about 200 psig are employed whereby optimum yields of sym-tet can be obtained in a batch reaction.

In another preferred embodiment, a mixture of chlorinated $\beta$-(trichloromethyl)pyridines, containing as a major portion 2,6-dichloro-3-(trichloromethyl)pyridine and/or 2-chloro-5-(trichloromethyl)pyridine, is employed as the chlorinated $\beta$-(trichloromethyl)pyridine starting material and reacted with chlorine in the presence of a catalyst at a temperature of from about 160° C. to about 200° C. and at a pressure of from about 100 psig to about 220 psig. The sym-tet prepared is then recovered by distillation. Similar results are obtained employing mixtures containing 2,3,6-trichloro-5-(trichloromethyl)pyridine and/or 2,3-dichloro-5-(trichloromethyl)pyridine.

In all embodiments of the present invention, it is to be noted that the only constraint placed upon the superatmospheric pressures employed is one of economics and that pressures in excess of the preferred 100–220 psig range may be employed.

The following examples illustrate the present invention and should not be construed as limiting its scope. All percentages are in weight percent unless indicated otherwise.

EXAMPLE 1

A mixture (778.6 grams) of chlorinated $\beta$-picolines containing 38.3 weight percent of 2,6-dichloro-3-(trichloromethyl)pyridine, 31.4 weight percent of 2-chloro-5-(trichloromethyl)pyridine, 17.9 weight percent of 2,3,6-trichloropyridine, 2.0 weight percent of 2,3,5,6-tetrachloropyridine, 2.0 weight percent of 2,3-dichloro-5-(trichloromethyl)pyridine, 0.4 weight percent of pentachloropyridine and 8.0 weight percent of other chlorinated $\beta$-picolines, together with 2.25 grams (0.4 mole %) of $FeCl_3$ catalyst, was chlorinated in the liquid phase in a Parr bomb at 200° C. and 200 psig by bubbling chlorine into the mixture at the rate of about 20.9 grams/hour. After 71.75 hours the reaction mixture contained the following:

|  | Wt. % |
|---|---|
| 2,3,5,6-tetrachloropyridine | 40.1 |
| 2,3,6-trichloropyridine | 38.1 |
| pentachloropyridine | 4.7 |
| other chlorinated pyridines | 14.4 |

The ratio of pentachloropyridine to 2,3,5,6-tetrachloropyridine was 0.12.

EXAMPLE 2–13

Substantially the same procedures conducted in Example 1 were repeated employing different mixtures of chlorinated $\beta$-picolines. The exact conditions are listed in Table I. The weight percent of the chlorinated $\beta$-picolines present in the starting mixture and product mixture is listed in Table I.

TABLE I

| Run No. | Starting Material, g | Average Mole % $FeCl_3$ | Temp °C. | Press. psig | $Cl_2$ Flow g/hr | Run Time, Hours | Weight Percent  |  |
|---|---|---|---|---|---|---|---|---|
| 2 | 442.0 | 1.0 | 200 | 200 | 16 | 0 | 13 | 2 |
|  |  |  |  |  |  | 48 | — | 57 |
| 3 | 648.6 | 0.36 | 200 | 200 | 18 | 0 | — | — |
|  |  |  |  |  |  | 12 | 8.4 | 2.6 |
|  |  |  |  |  |  | 24 | 12.8 | 10.5 |
| 4 | 1115.8 | 0.28 | 200 | 200 | 25 | 0 | 14.7 | 1.7 |
|  |  |  |  |  |  | 24 | 17.3 | 5.4 |
|  |  |  |  |  |  | 48 | 14.9 | 19.1 |
|  |  |  |  |  |  | 78 | 8.4 | 38.0 |
| 5 | 2231 | 0.28 | 185 | 200 | 18 | 0 | 13.6 | 1.6 |
|  |  |  |  |  |  | 12 | 14.0 | 2.1 |
|  |  |  |  |  |  | 30 | 13.5 | 2.3 |
|  |  |  |  |  |  | 55 | 16.8 | 4.4 |
|  |  |  |  |  |  | 103 | 18.7 | 7.7 |
|  |  |  |  |  |  | 169 | 19.0 | 19.4 |
| 6 | 2153.4 | 0.38 | 200 | 200 | 36 | 0 | 18.1 | 3.0 |
|  |  |  |  |  |  | 24 | 18.2 | 4.1 |
|  |  |  |  |  |  | 48 | 19.9 | 10.8 |
|  |  |  |  |  |  | 72 | 20.5 | 21.2 |
|  |  |  |  |  |  | 94 | 16.5 | 35.1 |
|  |  |  |  |  |  | 130 | 6.4 | 57.4 |

4,681,945
TABLE I-continued
| | | | | | | | | |
|---|---|---|---|---|---|---|---|---|
| 7 | 1124.8 | 0.56 | 200 | 200 | 29 | 0 | 17.7 | 8.9 |
| | | | | | | 24 | 23.5 | 15.2 |
| | | | | | | 42 | 27.9 | 24.8 |
| | | | | | | 69 | 22.5 | 41.4 |
| | | | | | | 92 | 17.9 | 54.6 |
| 8 | 2302.8 | 0.16 | 200 | 200 | 20 | 0 | 26.6 | 6.0 |
| | | | | | | 28 | 30.8 | 19.8 |
| | | | | | | 52 | 27.1 | 33.0 |
| | | | | | | 76 | 20.3 | 49.5 |
| 9 | 647.3 | 0.36 | 200 | 200 | 105 | 0 | — | — |
| | | | | | | 24 | — | 4.4 |
| | | | | | | 60 | — | 29.7 |
| | | | | | | 88 | — | 54.1 |
| 10 | 436.3 | 0.21 | 200 | 50 | 12 | 0 | — | 0.1 |
| | | | | | | 20 | — | 8.7 |
| | | | | | | 33 | — | 15.7 |
| | | | | | | 42 | — | 20.7 |
| 11 | 549.1 | 0.15 | 200 | 200 | 21 | 0 | — | — |
| | | | | | | 8 | — | 22 |
| | | | | | | 24 | — | 52.0 |
| 12 | 1194 | 0.31 | 200 | 200 | 7 | 0 | 17.3 | 1.7 |
| | | | | | | 25 | 20.2 | 3.4 |
| | | | | | | 51 | 24.2 | 10.5 |
| | | | | | | 72 | 23.0 | 20.0 |
| | | | | | | 92 | 19.4 | 31.6 |
| 13 | 1197.7 | 0.46 | 200 | 200 | 17 | 0 | 13.6 | 1.7 |
| | | | | | | 26 | 14.4 | 2.2 |
| | | | | | | 48 | 17.6 | 6.1 |
| | | | | | | 81 | 16.8 | 17.4 |
| | Weight Percent | | | | | |
|---|---|---|---|---|---|---|
| Run No. | 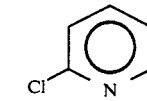 | 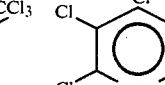 | 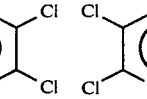 | 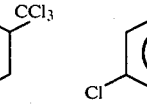 | 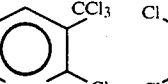 | Other |
| 2 | 32 | 0.4 | 2 | 26 | 1 | 24 |
| | 0.1 | 8 | 4 | 0.1 | 12 | 19 |
| 3 | 0.3 | 0.7 | 0.2 | 96.9 | 0.5 | 1.9 |
| | 0.2 | 0.7 | 0.3 | 63.8 | 13.0 | 11.0 |
| | 0.2 | 0.9 | 0.4 | 44.5 | 24.3 | 6.4 |
| 4 | 33.0 | 0.4 | 1.7 | 26.3 | 0.9 | 21.3 |
| | 7.6 | 1.2 | 13.2 | 29.9 | 7.9 | 17.5 |
| | 1.4 | 2.8 | 11.1 | 16.2 | 18.7 | 15.8 |
| | 0.2 | 5.3 | 7.4 | 5.1 | 20.9 | 14.5 |
| 5 | 35.1 | 0.3 | 1.7 | 31.7 | 0.9 | 15.1 |
| | 20.3 | 0.7 | 11.4 | 30.9 | 1.9 | 18.7 |
| | 11.4 | 0.9 | 16.2 | 32.6 | 3.1 | 20.0 |
| | 3.1 | 1.4 | 17.5 | 30.9 | 8.5 | 17.4 |
| | 1.5 | 1.5 | 15.9 | 25.9 | 12.2 | 16.6 |
| | 0.4 | 3.5 | 11.5 | 14.6 | 16.7 | 14.9 |
| 6 | 18.4 | 5.2 | 5.9 | 18.6 | 13.9 | 16.9 |
| | 12.2 | 5.3 | 8.3 | 20.8 | 13.4 | 17.7 |
| | 2.4 | 5.8 | 9.1 | 17.8 | 14.0 | 20.2 |
| | 0.5 | 7.0 | 6.1 | 9.9 | 13.5 | 21.3 |
| | — | 8.4 | 3.1 | 4.4 | 11.3 | 21.2 |
| | — | 11.1 | 1.2 | 0.7 | 6.8 | 16.4 |
| 7 | 28.7 | 1.2 | 2.5 | 22.5 | 7.4 | 11.1 |
| | 5.8 | 2.1 | 10.8 | 26.0 | 11.3 | 5.3 |
| | 1.2 | 3.1 | 7.9 | 16.9 | 12.6 | 5.6 |
| | — | 5.2 | 5.1 | 8.2 | 13.3 | 4.3 |
| | — | 6.5 | 3.1 | 3.5 | 9.9 | 4.5 |
| 8 | 5.0 | 0.9 | 10.1 | 34.7 | 7.9 | 8.8 |
| | 0.5 | 2.6 | 6.4 | 17.4 | 12.2 | 10.3 |
| | — | 3.9 | 3.9 | 8.3 | 11.0 | 12.8 |
| | — | 5.6 | 2.2 | 3.4 | 8.6 | 10.4 |
| 9 | — | 0.4 | 92.4 | — | — | 7.2 |
| | — | 0.5 | 68.4 | 0.2 | 19.5 | 7.0 |
| | — | 0.7 | 32.0 | — | 34.5 | 3.1 |
| | — | 1.1 | 17.2 | — | 24.1 | 3.5 |
| 10 | — | — | 96.1 | — | 0.2 | 3.6 |
| | — | 0.4 | 55.9 | — | 22.5 | 12.5 |
| | — | 0.6 | 43.4 | — | 31.4 | 8.9 |
| | — | 0.6 | 33.9 | — | 29.7 | 15.1 |
| 11 | — | — | — | — | 84.9 | 15.1 |
| | — | 0.6 | 0.2 | — | 58.2 | 13.2 |
| | — | 5.0 | — | — | 22.1 | 20.9 |
| 12 | 30.3 | — | 2.3 | 35.5 | 1.6 | 11.3 |
| | 6.9 | 0.5 | 10.8 | 39.5 | 6.1 | 12.6 |
| | 1.9 | 1.3 | 9.9 | 28.1 | 12.7 | 11.4 |
| | 0.6 | 2.1 | 7.2 | 15.8 | 14.3 | 17.0 |
| | 0.2 | 3.1 | 5.6 | 8.6 | 14.9 | 16.6 |

TABLE I-continued

| 13 | 31.7 | 0.4 | 1.8 | 26.4 | 0.9 | 21.5 |
| --- | --- | --- | --- | --- | --- | --- |
|  | 18.7 | 0.8 | 10.5 | 32.7 | 3.2 | 17.5 |
|  | 5.3 | 1.2 | 14.2 | 27.0 | 9.5 | 19.1 |
|  | 1.0 | 2.1 | 11.0 | 14.6 | 16.4 | 20.7 |

— indicates none detected

Intermediates formed during the present reaction, such as, for example 2,3,6-trichloro-5-(trichloromethyl)pyridine and 2,3,6-trichloropyridine are conveniently recycled for more complete conversion to sym-tet employing techniques well known in the art.

In other embodiments of the present invention, the reaction is conducted on a continuous recycle basis to prepare sym-tet. Such a process comprises the continuous chlorination of chlorinated β-(trichloromethyl)-pyridines at temperatures of at least about at least 160° C. and at pressures of from about atmospheric to about 220 psig or more. Such a continuous process is conducted employing well known apparatus and procedures such as those described in U.S. Pat. No. 4,256,894 which is incorporated herein by reference.

STARTING MATERIALS

Chlorine and chlorinated β-(trichloromethyl)pyridines employed as starting materials are all well known compounds. See, for example, U.S. Pat. Nos. 4,184,041; 4,288,599; 4,266,064; 4,241,213; and 4,205,175; Japanese Patent Disclosure 55-85564 (27 June 1980) and EPO Application 80201077.7 (Publication No. 0 028 870); all of which are incorporated herein by reference.

We claim:

1. A catalytic process of chlorinating a mixture rich in 2,6-dichloro-3-trichloromethyl pyridine to form a mixture rich in 2,5,6-trichloromethyl pyridine and 2,3,5,6-tetrachloro pyridine comprising:
   (a) establishing in a reactor means a reactor charge comprising a mixture rich in 2,6-dichloro-3-trichloro-methyl pyridine and a sufficient amount of ferric chloride catalyst; and
   (b) while maintaining the reactor charge in liquid phase at a temperature of at least about 160° C., feeding chlorine into and agitating the reactor charge for a sufficient time to catalytically convert the mixture rich in 2,6-dichloro-3-trichloromethyl pyridine to a mixture rich in 2,5,6-trichloro-3-trichloromethyl pyridine and 2,3,5,6-tetrachloro pyridine.

* * * * *

UNITED STATES PATENT AND TRADEMARK OFFICE
CERTIFICATE OF CORRECTION

PATENT NO. : 4,681,945
DATED : July 21, 1987
INVENTOR(S) : Paula L. Humphreys and Thomas L. Dietsche It is certified that error appears in the above-identified patent and that said Letters Patent is hereby corrected as shown below:

Column 8, line 14, Claim 1, after "in" the word should be --2,5,6-trichloro-3-trichloromethyl--.

Signed and Sealed this

Thirtieth Day of August, 1988

Attest:

DONALD J. QUIGG

Attesting Officer

Commissioner of Patents and Trademarks